United States Patent [19]

Li et al.

[11] Patent Number: 5,504,003
[45] Date of Patent: Apr. 2, 1996

[54] MACROPHAGE INFLAMMATORY PROTEIN-3 AND -4

[75] Inventors: Haodong Li, Germantown; Steven Ruben, Olney, both of Md.

[73] Assignee: Human Genome Sciences, Inc., Rockville, Md.

[21] Appl. No.: 208,339

[22] Filed: Mar. 8, 1994

[51] Int. Cl.⁶ .............................. C12N 5/10; C12N 15/12; C12P 21/06; A61K 38/00
[52] U.S. Cl. .................. 435/240.2; 435/69.1; 435/252.3; 435/172.3; 435/320.1; 424/85.2; 424/93.2; 424/93.21; 530/350; 530/351; 514/2; 514/12; 536/22.1; 536/23.1; 536/23.5; 935/57
[58] Field of Search ................... 424/85.2, 93.2, 424/93.21; 435/69.1, 240.2, 252.3, 320.1, 172.3; 530/350, 351; 514/2, 12; 536/22.1, 23.1, 23.5; 935/57

[56] References Cited

FOREIGN PATENT DOCUMENTS

| | | | |
|---|---|---|---|
| WO9002762 | 3/1990 | WIPO | A61K 37/02 |
| WO9205198 | 9/1991 | WIPO | C07K 15/00 |
| WO9200326 | 1/1992 | WIPO | A61K 37/66 |
| WO9200327 | 1/1992 | WIPO | A61K 37/66 |
| WO9213553 | 2/1992 | WIPO | A61K 37/02 |
| WO9309799 | 11/1992 | WIPO | A61K 37/02 |

OTHER PUBLICATIONS

Kwon et al., "cDNA sequences of two inducible T-cell genes," *Proc. Natl. Acad. Sci.*, USA vol. 86, pp. 1963–1967, Mar., 1989.
Nakao et al., "Structures of Human Genes Coding for Cytokine LD78 and Their Expression," *Mol. Cell. Biol.*, vol. 10, No. 7, pp. 3646–3658, Jul. 1990.

*Primary Examiner*—Keith C. Furman
*Assistant Examiner*—Hyosuk Kim
*Attorney, Agent, or Firm*—Elliot M. Olstein; Gregory D. Ferraro

[57] ABSTRACT

There is disclosed a human macrophage inflammatory protein-3 (MIP-3) and a human macrophage inflammatory protein-4 (MIP-4) polypeptides and DNA (RNA) encoding such polypeptides. There is also provided a procedure for producing such polypeptides by recombinant techniques and for producing antibodies against such polypeptides. In the invention there is also provided antagonist/inhibitors against such polypeptides which inhibit the functioning of such polypeptides. Another aspect of the invention provides a combination of the polypeptides of the present invention and a suitable pharmaceutical carrier for providing a therapeutically effective amount of the polypeptides for the treatment of various associated diseases.

34 Claims, 7 Drawing Sheets

```
  1 ATGAAGGTCTCCGTGGCTGCCCTCTCCTGCCTACATGCCTTTTTACTGCCCTTGGTCCCA  60
    M  K  V  S  V  A  A  L  S  C  L  H  A  F  L  L  P  L  V  P

61 GGGCCGGGTCACAAAAGATGCAGAGACAGAGTTCATGAATGTCAAAGCTTCCATTGGAAA 120
    G  P  G  H  K  R  C  R  D  R  V  H  E  C  Q  S  F  H  W  K

121 ATCCAGTACTTCTGGGACAGATTCCATGCTACTAGTGCTGACTGCTGCATCTCCTACACC 180
    I  Q  Y  F  W  D  R  F  H  A  T  S  A  D  C  C  I  S  Y  T

181 CCACGAAGCATCCCGTGTTCACTCCTGGAGAGTTACTTTGAAACGAACAGCGAGTGCTCC 240
    P  R  S  I  P  C  S  L  L  E  S  Y  F  E  T  N  S  E  C  S

241 AAGCCGGGTGTCATCTTCCTCACCAAGAAGGGGCGACGTTTCTGTGCCAACCCCAGTGAT 300
    K  P  G  V  I  F  L  T  K  K  G  R  R  F  C  A  N  P  S  D

301 AAGCAAGTTCAGGTTTGCATGAGAATGCTGAAGCTGGACACACGGATCAAGACCAGGAAG 360
    K  Q  V  Q  V  C  M  R  M  L  K  L  D  T  R  I  K  T  R  K

361 AATTGA 366
    N  *
```

FIG.1

```
1   ATGAAGGGCCTTGCAGCTGCCCTCCTTGTCCTCGTCTGCACCATGGCCCTCTGCTCCTGT   60
    M  K  G  L  A  A  A  L  L  V  L  V  C  T  M  A  L  C  S  C

61  GCACAAGTTGGTACCAACAAAGAGCTCTGCTGCCTCGTCTATACCTCCTGGCAGATTCCA   120
    A  Q  V  G  T  N  K  E  L  C  C  L  V  Y  T  S  W  Q  I  P

121 CAAAAGTTCATAGTTGACTATTCTGAAACCAGCCCCCAGTGCCCCAAGCCAGGTGTCATC   180
    Q  K  F  I  V  D  Y  S  E  T  S  P  Q  C  P  K  P  G  V  I

181 CTCCTAACCAAGAGAGGCCGGCAGATCTGTGCTGACCCCAATAAGAAGTGGGTCCAGAAA   240
    L  L  T  K  R  G  R  Q  I  C  A  D  P  N  K  K  W  V  Q  K

241 TACATCAGCGACCTGAAGCTGAATGCCTGA   270
    Y  I  S  D  L  K  L  N  A  *
```

FIG.2

```
  1  MKVSVAALSCLHAFLLPLVPGPGHKRCRDRVHECQSFHWKIQYFWDRFHA  50
     |.||.|||    |.||. ::  ..:                |...: |
  1  MQVSTAAL....AVLLCTMALCNQ....................FSASLAA  27

51  .TSADCCISYTPRSIPCSLLESYFETNSECSKPGVIFLTKKGRRFCANPS  99
     |...||:|||.| || .:...||||.|:|||||||||||::|..||:||
 28  DTPTACCFSYTSRQIPQNFIADYFETSSQCSKPGVIFLTKRSRQVCADPS  77

100  DKQVQVCMRMLKLDTRIKTRKN  125
     :. ||  ::. |.|..
 78  EEWVQKYVSDLELSA  92
```

FIG. 3

```
 1  MKGLAAALLVLVCTMALC....SCAQVGTNKELCCLVYTSWQIPQKFIVD  46
    |...|||  ||:|||||||    |.:  .:.... ||: |||:||||.||.|
 1  MQVSTAALAVLLCTMALCNQVLSAPLAADTPTACCFSYTSRQIPQNFIAD  50

47  YSETSPQCPKPGVILLTKRGRQICADPNKKWVQKYISDLKLNA  89
    | |||.||.||:||:|||||||:||||...|||||:|||.|.|
51  YFETSSQCSKPSVIFLTKRGRQVCADPSEEWVQKYVSDLELSA  93
```

FIG.4

MACROPHAGE INFLAMMATORY PROTEIN-3 AND -4

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human macrophage inflammatory protein-3 (MIP-3) and macrophage inflammatory protein-4 (MIP-4). The invention also relates to inhibiting the action of such polypeptides.

Macrophage inflammatory proteins (MIPs) are proteins that are produced by certain mammalian cells, for example, macrophages and lymphocytes, in response to stimuli, such as gram-negative bacteria, lipopolysaccharide and concanavalin A. Thus, the MIP molecules may have diagnostic and therapeutic utility for detecting and treating infections, cancer, inflammation, myelopoietic dysfunction, and autoimmune diseases.

Murine MIP-1 is a major secreted protein from lipopolysaccharide stimulated RAW 264.7, a murine macrophage tumor cell line. It has been purified and found to consist of two related proteins, MIP-1α and MIP-1β.

Several groups have cloned what are likely to be the human homologs of MIP-1α and MIP-1β. In all cases, cDNAs were isolated from libraries prepared against activated T-cell RNA.

The macrophage inflammatory proteins (MIP-1α and MIP-1β) have been shown to exhibit pro-inflammation properties. MIP-1α can induce migration and activation of human eosinophils and monocytes and induces the chemotaxis of macrophages. In addition, the murine MIP-1α has suppressive effects on human hematopoietic stem cell proliferation, while the murine MIP-1β can abrogate the inhibitory effect of MIP-1α. Finally, MIP-1 proteins can be detected in early wound inflammation cells and have been shown to induce production of IL-1 and IL-6 from wound fibroblast cells.

MIP-1s are part of the chemokine family which have numerous functions related to inflammation or wound healing, immunoregulation and play active roles in a number of disease conditions. Further, MIP-1 has been found to have hematopoietic potentiating effects. Broxmeyer, H. E., et al., J. Exp. Med., 170:1583–94 (1989) and Broxmeyer, H. E., et al., Blood, 76:1110–6 (1990)

The definition of the bioactivities of MIP-1 has been extensively studied and has utilized native MIP-1 and very recently recombinant MIP-1α and MIP-1β. Purified native MIP-1 (comprising MIP-1, MIP-1α and MIP-1β polypeptides) causes acute inflammation when injected either subcutaneously into the footpads of mice or intracisternally into the cerebrospinal fluid of rabbits (Wolpe and Cerami, 1989, FASEB J. 3:2565–73). In addition to these pro-inflammatory properties of MIP-1, which may be direct or indirect, MIP-1 has been recovered during the early inflammatory phases of wound healing in an experimental mouse model employing sterile wound chambers (Fahey, et al., 1990, Cytokine, 2:92). For example, PCT application U.S. Ser. No. 91/06489, filed by Chiron Corporation, discloses a DNA molecule which is active as a template for producing mammalian macrophage inflammatory proteins (MIPs) in yeast.

The murine MIP-1α and MIP-1β are distinct but closely related cytokines. Partially purified mixtures of the two proteins affect neutrophil function and cause local inflammation and fever. The particular properties of MIP-1α have been identified as being identical to an inhibitor of haemopoietic stem cell growth. MIP-1α has been expressed in yeast cells and purified to homogeneity. Structural analysis confirmed that MIP1α has a very similar secondary and tertiary structure to platelet factor 4 and interleukin 8 with which it shares limited sequence homology. MIP-1α has been found to have in vitro stem cell inhibitory properties. It has also been demonstrated that MIP-1α is active in vivo to protect mouse stem cells from subsequent in vitro killing by tritiated thymidine. MIP-1α was also shown to enhance the proliferation of more committed progenitor granulocyte macrophage colony-forming cells in response to granulocyte macrophage colony-stimulating factor. Clemens, J. M., et al., Cytokine, 4:76–82 (1992).

MIP-1α is a 6–8 kd, lipopolysaccharide inducible monocyte, neutrophil and eosinophil chemotactic protein. MIP-1α can also induce the migration and activation of human eosinophil granulocytes. MIP-1α may be important in acute and chronic inflammation. The sequential production, source, and in vivo contribution of murine MIP-1α in synchronized *schistosoma mansoni* during pulmonary granuloma formation has been determined. Lukacs, N. W., et al., J. Exp. Med., 177:1551–9 (1993).

In accordance with one aspect of the present invention, there are provided novel mature polypeptides which are MIP-3 and MIP-4, as well as analogs and derivatives thereof. The MIP-3 and MIP-4 of the present invention are of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, for example, immunoregulation including inflammatory activity, hematopoiesis and lymphocyte trafficking, inhibition of bone marrow stem cell colony formation, treatment of psoriasis, solid tumors, and enhancement of host defenses against resistant chronic infection.

In accordance with yet a further aspect of the present invention, there is provided an antibody against such polypeptides.

In accordance with yet another aspect of the present invention, there are provided antagonist/inhibitors to such polypeptides, which may be used to inhibit the action of such polypeptides, for example, in the treatment of arteriosclerosis, autoimmune and chronic inflammatory and infective diseases, histamine-mediated allergic reactions, hypereosinophilic syndrome, silicosis, sarcoidosis, inflammatory diseases of the lung, inhibition of IL 1 and TNF, aplastic anaemia, and myelodysplastic syndrome.

These and other aspects of the present invention should be apparent to those skilled in the art from the teachings herein.

The following drawings are illustrative of embodiments of the invention and are not meant to limit the scope of the invention as encompassed by the claims.

FIG. 1 displays the cDNA sequence encoding MIP-3 and the corresponding deduced amino acid sequence. The initial 45 amino acids represents the deduced putative leader sequence.

FIG. 2 displays the cDNA sequence encoding MIP-4 and the corresponding deduced amino acid sequence. The initial 19 amino acids represent a putative leader sequence.

FIG. 3 corresponds to a portion of the deduced amino acid sequence of MIP-3 in alignment with a portion of MIP-1α. The top sequence is human MIP-3 amino acid sequence and the bottom sequence is human MIP-1α (Human Tonsillar lymphocyte LD78 Beta protein precursor).

FIG. 4 displays two amino acid sequences wherein, the top sequence is the human MIP-4 amino acid sequence and the bottom sequence is human MIP-1α (Human Tonsillar lymphocyte LD78 Beta protein precursor).

Figure 5:
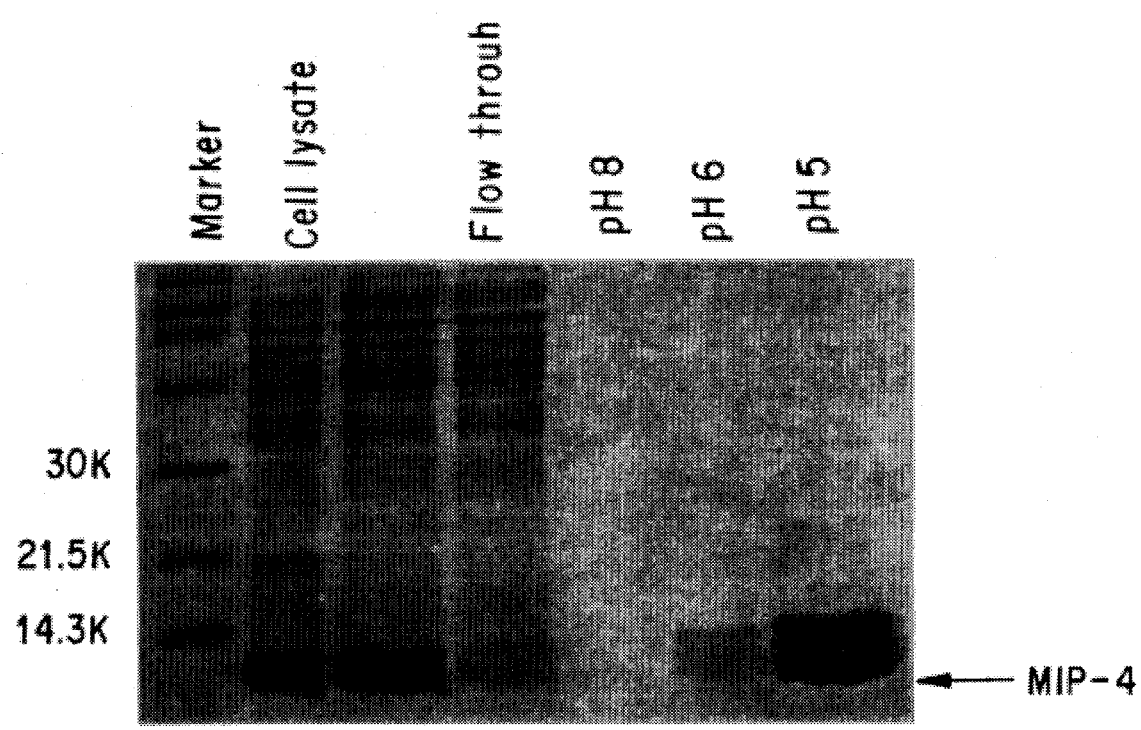
FIG. 5 shows the protein bands corresponding to the MIP-4 protein after expression in an E. coli bacterial expression system and purification.

In accordance with an aspect of the present invention, there are provided isolated nucleic acids (polynucleotides) which encode for the mature polypeptide having the deduced amino acid sequence of FIGS. 1 and 2 or for the mature MIP-3 polypeptide encoded by the cDNA of the clone(s) deposited as ATCC Deposit No. 75676 on Feb. 9, 1994, and for the mature MIP-4 polypeptide encoded by the cDNA of the clone depsoited as ATCC Deposit No. 75675 on Feb. 9, 1994.

Polynucleotides encoding polypeptides of the present invention are structurally related to the pro-inflammatory supergene "intercrine" which is in the cytokine or chemokine family. Both MIP-3 and MIP-4 are MIP-1 homologues and are more homologous to MIP-1α than to MIP-1β. The polynucleotide encoding for MIP-3 was derived from an aortic endothelium cDNA library and contains an open reading frame encoding a polypeptide of 121 amino acid residues, which exhibits significant homology to a number of chemokines. The top match is to the human macrophage inflammatory protein 1 alpha, showing 36% identity and 66% similarity (FIG. 3).

The polynucleotide encoding for MIP-4 was derived from an adult lung cDNA library and contains an open reading frame encoding a polypeptide of 89 amino acid residues, which exhibits significant homology to a number of chemokines. The top match is to the human tonsillar lymphocyte LD78 beta protein, showing 60% identity and 89% similarity (FIG. 4). Furthermore, the four cysteine residues occurring in all chemokines in a characteristic motif are conserved in both clone(s). The fact that the first two cysteine residues in our gene are in adjacent positions classifies it as "C—C" or β subfamily of chemokines. In the other subfamily, the "CXC" or α subfamily, the first two cysteine residues are separated by one amino acid.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in FIG. 1 and 2 or that of the deposited clone(s) or may be a different coding sequence which coding sequence, as a result of the redundancy or degeneracy of the genetic code, encodes the same, mature polypeptides as the DNA of FIG. 1 and 2 or the deposited cDNA.

The polynucleotides which encode for the mature polypeptides of FIGS. 1 and 2 or for the mature polypeptides encoded by the deposited cDNA may include: only the coding sequence for the mature polypeptide; the coding sequence for the mature polypeptides and additional coding sequence such as a leader or secretory sequence or a proprotein sequence; the coding sequence for the mature polypeptides (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1 and 2 or the polypeptides encoded by the cDNA of the deposited clone(s). The variants of the polynucleotides may be a naturally occurring allelic variant of the polynucleotides or a non-naturally occurring variant of the polynucleotides.

Thus, the present invention includes polynucleotides encoding the same mature polypeptides as shown in FIGS. 1 and 2 or the same mature polypeptides encoded by the cDNA of the deposited clone(s) as well as variants of such polynucleotides which variants encode for a fragment, derivative or analog of the polypeptides of FIG. 1 and 2 or the polypeptides encoded by the cDNA of the deposited clone(s). Such nucleotide variants include deletion variants, substitution variants and addition or insertion variants.

As hereinabove indicated, the polynucleotide may have a coding sequence which is a naturally occurring allelic variant of the coding sequence shown in FIG. 1 and 2 or of the coding sequence of the deposited clone(s). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with description of sequences herein. A license may be required to make, use or sell the deposited materials, and no such license is hereby granted.

The present invention further relates to MIP-3 and MIP4 polypeptides which have the deduced amino acid sequence of FIGS. 1 and 2 or which have the amino acid sequence encoded by the deposited cDNA, as well as fragments, analogs and derivatives of such polypeptide.

The terms "fragment," "derivative" and "analog" when referring to the polypeptides of FIGS. 1 and 2 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptides of the present invention may be a recombinant polypeptide, a natural polypeptide or a synthetic polypeptide, preferably a recombinant polypeptide.

The fragment, derivative or analog of the polypeptides of FIGS. 1 and 2 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptides are fused with another compound, such as a compound to increase the half-life of the polypeptide (for example, polyethylene glycol), or (iv) one in which the additional amino acids are fused to the mature polypeptides, such as a leader or secretory sequence or a sequence which is employed for purification of the mature polypeptides or a proprotein sequence. Such fragments, derivatives and analogs are deemed to be within the scope of those skilled in the art from the teachings herein.

The polypeptides of the present invention are preferably provided in an isolated form, and preferably are purified to homogeneity.

The term "isolated" means that the material is removed from its original environment (e.g., the natural environment if it is naturally occurring). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the MIP-3 and MIP-4 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long they are replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella Typhimurium; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. Coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, WI, USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5'flanking nontranscribed sequences. DNA sequences derived from the SV40 splice, and polyadenylation sites may be used to provide the required nontranscribed genetic elements.

MIP-3 and MIP-4 are recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification. (Price et al., J. Biol. Chem., 244:917 (1969). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be nonglycosylated. Polypeptides of the invention may also include an initial methionine amino acid residue.

The polypeptides of the present invention may be used in a variety of immunoregulatory and inflammatory functions and also in a number of disease conditions. MIP-3 and MIP-4 are in the chemokine family and therefore they are a chemo-attractant for leukocytes (such as monocytes, neutrophils, T lymphocytes, eosinophils, basophils, etc.). Accordingly, MIP-3 and MIP-4 can be used to facilitate wound healing by controlling infiltration of target immune cells to the wound area. In a similar fashion, the polypeptides of the present invention can enhance host defenses against chronic infections, e.g., mycobacterial, via the attraction and activation of microbicidal leukocytes.

Further, the polypeptides of the present invention may be useful in anti-tumor therapy since there is evidence that chemokine expressing cells injected into tumors have caused regression of the tumor, for example, in the treatment of Kaposi sarcoma. Also, MIP-3 and MIP-4 stimulate the invasion and activation of host defense (tumoricidal) cells, e.g., cytotoxic T-cells and macrophages, and in this way may also be used to treat solid tumors.

The polypeptides may also be useful to inhibit bone marrow stem cell colony formation for leukemia and as adjunct protective treatment of hematopoietic stem cells during cancer chemotherapy.

Another use of the polypeptides is the inhibition of T-cell proliferation via inhibition of IL-2 biosynthesis, for example, in auto-immune disease and lymphocytic leukemia.

MIP-3 and MIP-4 may also be useful for inhibiting epidermal keratinocyte proliferation which has utility in psoriasis (keratinocyte hyper-proliferation) since Langerhans cells in skin have been found to produce MIP-1α.

MIP-3 and MIP-4 may be used to prevent prevent scarring during wound healing both via the recruitment of debris-cleaning and connective tissue-promoting inflammatory cells and by its possible control of excessive TGFβ-mediated fibrosis, in addition these polypeptides may be used to treat stroke, thrombocytosis, pulmonary emboli and myeloproliferative disorders, since MIP-3 and MIP-4 increase vascular permeability.

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptides. Such methods are well-known in the art. For example, cells may be engineered by procedures known in the art by use of a retroviral particle containing RNA encoding the polypeptides of the present invention.

Similarly, cells may be engineered in vivo for expression of a polypeptides in vivo by, for example, procedures known in the art. As known in the art, a producer cell for producing a retroviral particle containing RNA encoding the polypeptides of the present invention may be administered to a patient for engineering the cells in vivo and expression of the polypeptides in vivo. These and other methods for administering polypeptides of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The polypeptides of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, intravenous, intraperitoneal, intramuscular, subcutaneous, intranasal or intradermal routes. The amounts and dosage regimens of MIP-3 and MIP-4 administered to a subject will depend on a number of factors such as the mode of administration, the nature of the condition being treated and the judgment of the prescribing physician. Generally speaking, they are given, for example, in therapeutically effective doses of at least about 10 µg/Kg body weight and in most cases they will be administered in an amount not in excess of about mg/Kg body weight per day and preferably the dosage is from about 10 µg/Kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting MIP-3 and MIP-4 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of MIP-3 and MIP-4. The antisense RNA oligonucleotide hybridizes to the mRNA in vivo and blocks translation of the mRNA molecule into the MIP-3 and MIP-4 (antisense—Okano, J. Neurochem., 56:560 (1991); Oligodeoxynucleotides as Antisense Inhibitors of Gene Expression, CRC Press, Boca Raton, FL (1988).

Alternatively, the oligonucleotides described above can be delivered to cells by procedures in the art such that the antisense RNA or DNA may be expressed in vivo to inhibit production of MIP-3 and MIP-4 in the manner described above.

Accordingly, antisense constructs to the MIP-3 and MIP4 can be used to treat disorders which are either MIP-induced or enhanced, for example, atherosclerosis, auto-immune, e.g. multiple sclerosis and insulin-dependent diabetes, and chronic inflammatory and infective diseases, histamine-mediated allergic reactions, rheumatoid arthritis, silicosis, sarcoidosis, idiopathic pulmonary fibrosis and other chronic inflammatory diseases of the lung, idiopathic hyper-eosinophilic syndrome, endotoxic shock, histamine-mediated allergic reactions, prostaglandin-independent fever, and aplastic anemia and other cases of bone marrow failure.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain and humanized antibodies, as well as Fab fragments, or the product of an Fab expression library. Various procedures known in the art may be used for the production of such antibodies and fragments.

Antibodies generated against the polypeptides corresponding to a sequence of the present invention or its in vivo receptor can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptides from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptides products of this invention.

The present invention is also directed to antagonist/inhibitors of the polypeptides of the present invention, which inhibit or eliminate the function of the polypeptide.

Thus, for example, antagonists bind to a polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the polypeptide and thereby prevent the action of MIP-3 and MIP-4 since receptor sites are occupied.

In these ways, the antagonist/inhibitors may be used as an anti-inflammation drug, by preventing the attraction and activation of leukocytes. They may also be useful for inhibiting the chemotaxis and activation of macrophages and their precursors, and of neutrophils, basophils, B lymphocytes and some T-cell subsets, in auto-immune and chronic inflammatory and infective diseases; inhibiting MIP-induced mast cell and basophil degranulation and, hence, reduction in histamine-mediated allergic reactions; inhibiting deleterious cascades attributed primarily to IL-1 and TNF whose biosynthesis is stimulated by MIPs; rheumatoid arthritis; and preventing MIP-driven transition from predominantly neutrophilic inflammation to the macrophage-dominant pathology which may be a key switch from acute, resolving inflammatory defenses to chronic, ultimately destructive, mechanisms, e.g. auto-immune diseases.

These antagonist/inhibitors may also be useful for treating silicosis, sarcoidosis, idiopathic pulmonary fibrosis and other chronic inflammatory diseases of the lung; idiopathic hyper-eosinophilic syndrome since elevated MIP production exacerbates eosinophil production and migration; endotoxic shock caused by elevated levels of MIP in response to endotoxins; histamine-mediated allergic reactions by inhibiting MIP-induced mast cell and basophil degranulation; inhibition of prostaglandin-independent fever induced by MIP-1α; and preventing suppressive effects of excess MIP-1α in aplastic anemia and other cases of bone marrow failure.

The antibodies would also be useful for prognostic applications and clinical screening to track disease progression and the efficacy of therapeutic intervention. Resident macrophages produce little or no MIP mRNA, diagnostic antibodies able to detect this would be useful indicators of auto-immune disease and chronic inflammatory and infective states.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed-by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Figure 6:
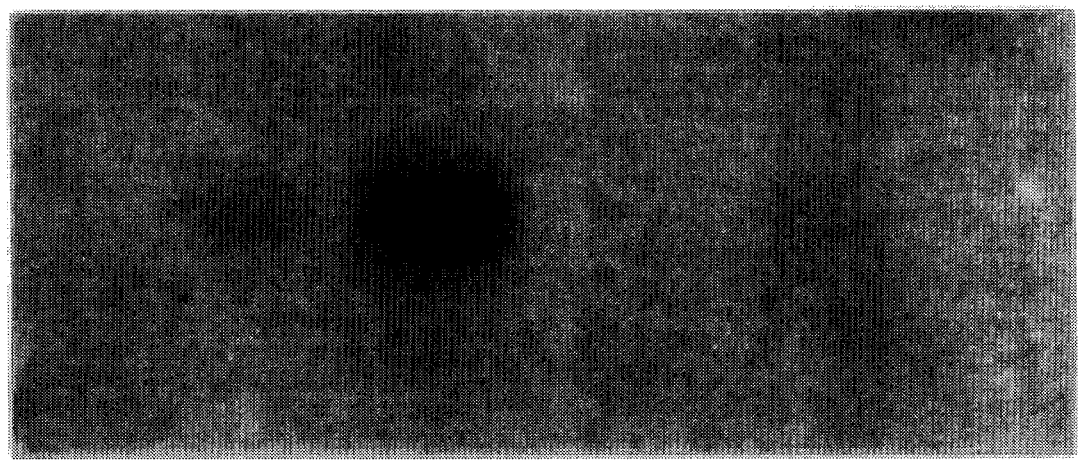
FIG. 6 is a northern blot analysis of the MIP-4 which indicates the cells in which this protein is most commonly found.
Figure 7:
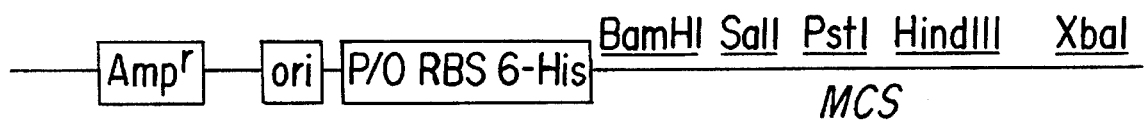
FIG. 7 is a schematic representation of the pQE-9 vector.

Bacterial Expression and Purification of MIP-3 The DNA sequence encoding for MIP-3, of clone HAECD08 (ATCC #75676) is initially amplified using PCR oligonucleotide primers corresponding to the 5' and sequences of the processed MIP-3 protein (minus the signal peptide sequence) and the vector sequences 3' to the MIP-3 gene. Additional nucleotides corresponding to Bam HI and XbaI were added to the 5' and 3' sequences respectively. The 5' oligonucleotide primer has the sequence 5'-TCAGGATCCGTCA-CAAAAGATGCAGA-3' contains a BamHI restriction enzyme site followed by 18 nucleotides of MIP-3 coding sequence starting from the presumed terminal amino acid of the processed protein codon. The 3' sequence 3' CGCTCTA-GAGTAAAACGACGGCCAGT-5' contains complementary sequences to XbaI site and to a pBluescript SK- vector sequence located 3' to the MIP-3 DNA insert. The restriction enzyme sites correspond to the restriction enzyme sites on the bacterial expression vector PQE-9. (Qiagen, Inc. 9259 Eton Avenue, Chatsworth, Calif., 91311). PQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into PQE-9 and are inserted in frame with the sequence encoding for the histidine tag and the RBS. FIG. 6 shows a schematic representation of this arrangement. The ligation mixture is then used to transform E. coli strain M15/rep4 available from Qiagen under the trademark M15/rep 4. M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized MIP-3 is purified from this solution by chromatography on a Nickel-Chelate column under conditions that allow for tight binding by proteins containing the 6-His tag. Hochuli, E. et al., J. Chromatography 411:177–184 (1984). MIP-3 (95% pure) is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate. The presence of a new protein corresponding to 14 kd following induction demonstrated expression of the MIP-3.

EXAMPLE 2

Bacterial Expression and Purification Of MIP-4

The DNA sequence encoding for MIP-4, of clone HAPAT57 (ATCC #75675) was initially amplified using PCR oligonucleotide primers corresponding to the 5' sequences of the processed MIP-4 protein (minus the signal peptide sequence) and sequences in the pBSK vector 3' to MIP-4 gene. Additional nucleotides corresponding to Bam HI and XbaI were added to the 5' and 3' sequences respectively. The 5' oligonucleotide primer has the sequence TCAGGATCCTGTGCACAAGTTGGTACC contains a BamHI restriction enzyme site followed by 18 nucleotides of MIP-4 coding sequence starting from the presumed terminal amino acid of the processed protein codon; The 3' sequence CGCTCTAGAGTAAAACGACGGCCAGT contains complementary sequences to XbaI site and to a pBluescript SK-vector sequence located 3' to the MIP-4 DNA insert. The restriction enzyme sites correspond to the restriction enzyme sites on the bacterial expression vector pQE-9 (Qiagen, Inc. 9259 Eton Avenue, Chatsworth, CA, 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI and XbaI The amplified sequences were ligated into pQE-9 and were inserted in frame with the sequence encoding for the histidine tag and the RBS. FIG. 6 shows a schematic representation of this arrangement. The ligation mixture was then used to transform E. coli strain available from Qiagen under the trademark M15/rep 4. M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized MIP-4 was purified from this solution by chromatography on a Nickel-Chelate column under conditions that allow for tight binding by proteins containing the 6-His tag. Hochuli, E. et al., J. Chromatography 411:177–184 (1984). MIP-4 (95% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate. The presence of a new protein corresponding to 14 kd following induction demonstrated expression of the MIP-4. (FIG. 5).

EXAMPLE 3

Expression of Recombinant MIP-3 in COS cells

The expression of plasmid, CMV-MIP-3 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire MIP-3 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follow:

The DNA sequence of clone HAECD08 (ATCC #75676), encoding for MIP-3 is constructed by PCR on the original EST cloned using two primers: the 5' primer (5'GGAAAGCTTATGAAGGTCTCCGTGGCT-3') contains a HindIII site followed by 18 nucleotides of MIP-3 coding sequence starting from the initiation codon; the 3' sequence (5'-CGCTCTAGATCAAGCGTAGTCTGG-GACGTCGTATGGGTAATTCTTCCTGGTCTTGATCC -3') contains complementary sequences to Xba I site, translation stop codon, HA tag and the last 20 nucleotides of the MIP-3 coding sequence (not including the stop codon). Therefore, the PCR product contains a HindIII site, MIP-3 coding sequence followed by HA tag fused in frame, a translation termination stop codon next to the HA tag, and an XbaI site. The PCR amplified DNA fragment and the vector, pcDNAI/Amp, are digested with HindIII and XbaI restriction enzyme and ligated. The ligation mixture is transformed into E. coli strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant MIP-3, COS cells are transfected with the expression vector by DEAE-DEXTRAN method.

(J. Sambrook, E. Fritsch, T. Maniatis, Molecular Cloning: A Laboratory Manual, Cold Spring Laboratory Press, (1989)). The expression of the MIP-3-HA protein is detected by radiolabelling and immunoprecipitation method. (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4

Expression of Recombinant MIP-4 in COS cells

The expression of plasmid, CMV-MIP-4 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire MIP-4 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follow:

The DNA sequence of clone HAPAT57 (ATCC #75675), encoding for MIP-4 is constructed by PCR on the original EST cloned using two primers: the 5' primer (5' GGAAAGCTTATGAAGGGCCTTGCAGCTGCC 3') contains a HindIII site followed by 20 nucleotides of MIP-4 coding sequence starting from the initiation codon; the 3' sequence (5' CGCTCTAGATCAABCGTAGTCTGG-GACGTCGTATGGGTAGGCATTCAGCTTCAGGTC 3') contains complementary sequences to Xba I site, translation stop codon, HA tag and the last 19 nucleotides of the MIP-4 coding sequence (not including the stop codon). Therefore, the PCR product contains a HindIII site, MIP-4 coding sequence followed by HA tag fused in frame, a translation termination stop codon next to the HA tag, and an XbaI site. The PCR amplified DNA fragment and the vector, pcDNAI/Amp, are digested with HindIII and XbaI restriction enzyme and ligated. The ligation mixture is transformed into E. coli strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant MIP-4, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989). The expression of the MIP-4-HA protein is detected by radiolabelling and immunoprecipitation method. (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 5

Expression pattern of MIP-3 in human tissue

Northern blot analysis was carried out to examine the levels of expression of MIP-3 in human tissues. Total cellular RNA samples were isolated with RNAzol™ B system (Biotecx Laboratories, Inc. 6023 South Loop East, Houston, Tex. 77033). About 10 ug of total RNA isolated from each human tissue specified is separated on 1% agarose gel and blotted onto a nylon filter. (Sambrook, Fritsch, and Maniatis, Molecular Cloning, Cold Spring Harbor Press, (1989), The labeling reaction is done according to the Stratagene Prime-It kit with 50 ng DNA fragment. The labeled DNA is purified with a Select-G-50 column. (5 Prime-3 Prime, Inc. 5603 Arapahoe Road, Boulder, CO 80303). The filter is then hybridized with radioactive labeled full length MIP-3 gene at 1,000,000 cpm/ml in 0.5M NaPO$_4$, pH 7.4 and 7% SDS overnight at 65° C. After wash twice at room temperature and twice at 60° C. with 0.5× SSC, 0.1% SDS, the filter is then exposed at −70° C. overnight with an intensifying screen.

EXAMPLE 6

Expression pattern of MIP-4 in human cells

Northern blot analysis was carried out to examine the levels of expression of MIP-4 in human cells. Total cellular RNA samples were isolated with RNAzol™ B system (Biotecx Laboratories, Inc. 6023 South Loop East, Houston, Tex. 77033). About 10 ug of total RNA isolated from each human tissue specified was separated on 1% agarose gel and blotted onto a nylon filter. (Sambrook, Fritsch, and Maniatis, Molecular Cloning, Cold Spring Harbor Press, (1989). The labeling reaction was done according to the Stratagene Prime-It kit with 50 ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length MIP-4 gene at 1,000,000 cpm/ml in 0.5M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. See FIG. 6.

Numerous modifications and variations of the present invention are possible in light of the above teachings and, therefore, within the scope of the appended claims, the invention may be practiced otherwise than as particularly described.

What is claimed is:

1. An isolated polynucleotide comprising a member selected from the group consisting of:

a polynucleotide encoding the polypeptide comprising the amino acid sequence as set forth in SEQ ID NO:4;

a polynucleotide encoding the polypeptide comprising amino acid 1 to amino acid 70 as set forth in SEQ ID NO:4; and a polynucleotide capable of hybridizing to and which is at least 95% identical to the polynucleotide of (a) or (b).

2. The polynucleotide of claim 1 wherein said polynucleotide is polynucleotide (c).

3. The polynucleotide of claim 1 encoding a polypeptide comprising the amino acid sequence as set forth in SEQ ID NO:4.

4. The polynucleotide of claim 1 encoding a polypeptide comprising amino acid 1 to amine acid 70 as set forth in SEQ ID NO:4.

5. An isolated polynucleotide comprising a polynucleotide encoding mature MIP-4.

6. An isolated polynucleotide comprising a member selected from the group consisting of:

(a) a polynucleotide encoding a mature polypeptide encoded by the DNA contained in ATCC Deposit No. 75675;

(b) a polynucleotide encoding the polypeptide encoded by the DNA contained in ATCC Deposit No. 75675; and (c) a polynucleotide capable of hybridizing to and which is at least 95% identical to the polynucleotide of (a) or (b).

7. The polynucleotide of claim 6 wherein the polynucleotide encodes a mature polypeptide encoded by the DNA contained in ATCC Deposit No. 75675.

8. The polynucleotide of claim 1 wherein the polynucleotide is DNA.

9. The polynucleotide of claim 1 wherein the polynucleotide is RNA.

10. The polynucleotide of claim 1 wherein the polynucleotide is genomic DNA.

11. The polynucleotide of claim 1 wherein the polynucleotide comprises nucleotide 1 to 270 of SEQ ID NO:3.

12. The polynucleotide of claim 1 wherein the polynucleotide comprises nucleotide 55 to 270 of SEQ ID NO:3.

13. A recombinant vector containing the DNA of claim 1.
14. A recombinant vector containing the DNA of claim 2.
15. A recombinant vector containing the DNA of claim 3.
16. A recombinant vector containing the DNA of claim 4.
17. A recombinant vector containing the DNA of claim 5.
18. A recombinant vector containing the DNA of claim 6.
19. A recombinant vector containing the DNA of claim 7.
20. A recombinant vector containing the DNA of claim 8.
21. A recombinant vector containing the DNA of claim 10.
22. A recombinant vector containing the DNA of claim 11.
23. A recombinant vector containing the DNA of claim 12.
24. A host cell containing the vector of claim 13.
25. A host cell containing the vector of claim 14.
26. A host cell containing the vector of claim 15.
27. A host cell containing the vector of claim 16.
28. A host cell containing the vector of claim 17.
29. A host cell containing the vector of claim 18.
30. A host cell containing the vector of claim 19.
31. A host cell containing the vector of claim 20.
32. A host cell containing the vector of claim 21.
33. A host cell containing the vector of claim 22.
34. A host cell containing the vector of claim 23.

\* \* \* \* \*

UNITED STATES PATENT AND TRADEMARK OFFICE
CERTIFICATE OF CORRECTION

PATENT NO.    : 5,504,003
DATED         : April 2, 1996
INVENTOR(S)   : Haodong Li, Germantown, MD; Steven Ruben, Olney, MD.

It is certified that an error appears in the above-identified patent and that said Letters Patent is hereby corrected as shown below:

Delete Claim 1 and replace with the following corrected claim wherein the additions are underlined:

--1. An isolated polynucleotide comprising a member selected from the group consisting of:

(a) a polynucleotide encoding the polypeptide comprising the amino acid sequence as set forth in SEQ ID NO:4;

(b) a polynucleotide encoding the polypeptide comprising amino acid 1 to amino acid 70 as set forth in SEQ ID NO:4; and (c) a polynucleotide capable or hybridizing to and which is at least 95% identical to the polynucleotide of (a) or (b). --

Signed and Sealed this

Eleventh Day of February, 1997

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
 ( A ) LENGTH: 366 BASE PAIRS
 ( B ) TYPE: NUCLEIC ACID
 ( C ) STRANDEDNESS: SINGLE
 ( D ) TOPOLOGY: LINEAR ( i i ) MOLECULE TYPE: cDNA ( x i ) SEQUENCE DESCRIPTION: SEQ ID NO:1:

```
ATGAAGGTCT CCGTGGCTGC CCTCTCCTGC CTACATGCCT TTTTACTGCC CTTGGTCCCA      60
GGGCCGGGTC ACAAAAGATG CAGAGACAGA GTTCATGAAT GTCAAAGCTT CATTGGAAAG     120
ATCCAGTACT TCTGGGACAG ATTCCATGCT ACTAGTGCTG ACTGCTGCAT CTCCTACACC     180
CCACGAAGCA TCCCGTGTTC ACTCCTGGAG AGTTACTTTG AAACGAACAG CGAGTGCTCC     240
AAGCCGGGTG TCATCTTCCT CACCAAGAAG GGGCGACGTT TCTGTGCCAA CCCCAGTGAT     300
AAGCAAGTTC AGGTTTGCAT GAGAATGCTG AAGCTGGACA CACGGATCAA GACCAGGAAG     360
AATTGA                                                                366
```

( 2 ) INFORMATION FOR SEQ ID NO:2:

( i ) SEQUENCE CHARACTERISTICS:
  ( A ) LENGTH: 121 AMINO ACIDS
  ( B ) TYPE: AMINO ACID
  ( C ) STRANDEDNESS:
  ( D ) TOPOLOGY: LINEAR ( i i ) MOLECULE TYPE: PROTEIN ( x i ) SEQUENCE DESCRIPTION: SEQ ID NO:2:

```
Met  Lys  Val  Ser  Val  Ala  Ala  Leu  Ser  Cys  Leu  His  Ala  Phe  Leu
-45            -40                      -35
Leu  Pro  Leu  Val  Pro  Gly  Pro  Gly  His  Lys  Arg  Cys  Arg  Asp  Arg
-30            -25                      -20
Val  His  Glu  Cys  Gln  Ser  Phe  His  Trp  Lys  Ile  Gln  Tyr  Phe  Trp
-15            -10                       -5
Asp  Arg  Phe  His  Ala  Thr  Ser  Ala  Asp  Cys  Cys  Ile  Ser  Tyr  Thr
 1              5                        10                            15
Pro  Arg  Ser  Ile  Pro  Cys  Ser  Leu  Leu  Gln  Ser  Tyr  Phe  Glu  Thr
               20                        25                            30
Asn  Ser  Glu  Cys  Ser  Lys  Pro  Gly  Val  Ile  Phe  Leu  Thr  Lys  Lys
               35                        40                            45
Gly  Arg  Arg  Phe  Cys  Ala  Asn  Pro  Ser  Asp  Lys  Gln  Val  Gln  Val
                    50                        55                       60
Cys  Met  Arg  Met  Leu  Lys  Leu  Asp  Thr  Arg  Ile  Lys  Thr  Arg  Lys
                    65                        70                       75
Asn
```

( 2 ) INFORMATION FOR SEQ ID NO:3:

( i ) SEQUENCE CHARACTERISTICS:
  ( A ) LENGTH: 270 BASE PAIRS
  ( B ) TYPE: NUCLEIC ACID
  ( C ) STRANDEDNESS: SINGLE
  ( D ) TOPOLOGY: LINEAR ( i i ) MOLECULE TYPE: cDNA ( x i ) SEQUENCE DESCRIPTION: SEQ ID NO:3:

```
ATGAAGGGCC TTGCAGCTGC CCTCCTTGTC CTCGTCTGCA CCATGGCCCT CTGCTCCTGT     60
GCACAAGTTG GTACCAACAA AGAGCTCTGC TGCCTCGTCT ATACCTCCTG GCAGATTCCA    120
CAAAAGTTCA TAGTTGACTA TTCTGAAACC AGCCCCCAGT GCCCCAAGCC AGGTGTCATC    180
CTCCTAACCA AGAGAGGCCG GCAGATCTGT GCTGACCCCA ATAAGAAGTG GGTCCAGAAA    240
```

TACATCAGCG ACCTGAAGCT GAATGCCTGA                                           270

( 2 ) INFORMATION FOR SEQ ID NO:4:

( i ) SEQUENCE CHARACTERISTICS:
        ( A ) LENGTH: 89 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:4:

```
Met  Lys  Gly  Leu  Ala  Ala  Ala  Leu  Leu  Val  Leu  Val  Cys  Thr  Met
               -15                      -10                         -5

Ala  Leu  Cys  Ser  Cys  Ala  Gln  Val  Gly  Thr  Asn  Lys  Glu  Leu  Cys
                     1                   5                        10

Cys  Leu  Val  Tyr  Thr  Ser  Trp  Gln  Ile  Pro  Gln  Lys  Phe  Ile  Val
                15                  20                        25

Asp  Tyr  Ser  Glu  Thr  Ser  Pro  Gln  Cys  Pro  Lys  Pro  Gly  Val  Ile
                30                       35                       40

Leu  Leu  Thr  Lys  Arg  Gly  Arg  Gln  Ile  Cys  Ala  Asp  Pro  Asn  Lys
                45                       50                       55

Lys  Trp  Val  Gln  Lys  Tyr  Ile  Ser  Asp  Leu  Lys  Leu  Asn  Ala
                60                       65                       70
```